(12) United States Patent
Lunsford et al.

(10) Patent No.: US 7,344,536 B1
(45) Date of Patent: *Mar. 18, 2008

(54) ELECTROCAUTERY SURGICAL SCISSORS

(75) Inventors: John P Lunsford, San Carlos, CA (US); Michael C Stewart, San Jose, CA (US)

(73) Assignee: Origin Medsystems, Inc., Santa Clara, CA (US)

( * ) Notice: Subject to any disclaimer, the term of this patent is extended or adjusted under 35 U.S.C. 154(b) by 217 days.

This patent is subject to a terminal disclaimer.

(21) Appl. No.: 10/851,051

(22) Filed: May 21, 2004

Related U.S. Application Data

(63) Continuation of application No. 10/071,940, filed on Feb. 5, 2002, now Pat. No. 6,749,609.

(51) Int. Cl.
*A61B 18/18* (2006.01)

(52) U.S. Cl. .................... 606/48; 606/41; 606/51

(58) Field of Classification Search .......... 606/27–52
See application file for complete search history.

(56) References Cited

U.S. PATENT DOCUMENTS

| | | | |
|---|---|---|---|
| 5,171,256 A | 12/1992 | Smith et al. | |
| 5,184,625 A | 2/1993 | Cottone, Jr. et al. | |
| 5,320,636 A | 6/1994 | Slater | |
| 5,324,289 A | 6/1994 | Eggers | |
| 5,338,317 A | 8/1994 | Hasson et al. | |
| 5,342,381 A | 8/1994 | Tidemand | |
| 5,352,222 A | 10/1994 | Rydell | |
| 5,356,408 A | 10/1994 | Rydell | |
| 5,366,476 A | 11/1994 | Noda | |
| 5,392,789 A | 2/1995 | Slater et al. | |
| 5,395,386 A | 3/1995 | Slater | |
| 5,396,900 A | 3/1995 | Slater et al. | |
| 5,514,134 A | 5/1996 | Rydell et al. | |
| 5,531,755 A | 7/1996 | Smith et al. | |
| 5,540,685 A | 7/1996 | Parins et al. | |
| 5,540,711 A | 7/1996 | Kieturakis et al. | |
| 5,549,606 A | 8/1996 | McBrayer et al. | |
| 5,569,243 A | 10/1996 | Kortenbach et al. | |
| 5,571,100 A | 11/1996 | Goble et al. | |
| 5,591,202 A | 1/1997 | Slater et al. | |
| 5,666,965 A | 9/1997 | Bales et al. | |
| 5,690,606 A | 11/1997 | Slotman | |
| 5,695,521 A | 12/1997 | Anderhub | |
| 5,697,949 A | 12/1997 | Giurtino et al. | |
| 5,700,261 A | 12/1997 | Brinkerhoff | |
| 5,707,392 A | 1/1998 | Kortenbach | |
| 5,741,285 A | 4/1998 | McBrayer et al. | |
| 5,779,701 A | 7/1998 | McBrayer et al. | |
| 5,849,022 A | 12/1998 | Sakashita et al. | |
| 5,860,975 A * | 1/1999 | Goble et al. | 606/45 |
| 5,891,140 A * | 4/1999 | Ginn et al. | 606/48 |
| 5,893,846 A | 4/1999 | Bales et al. | |

(Continued)

Primary Examiner—Roy D. Gibson
Assistant Examiner—Pete Vrettakos
(74) Attorney, Agent, or Firm—Fenwick & West LLP

(57) ABSTRACT

Surgical apparatus includes bipolar electrodes and tissue-shearing blades configured to electrically contact tissue for electrocauterization thereof prior to shearing contact of the cutting blades with the tissue over wide angles of presentation of the tissue to the electrodes and blades. Extensions or protrusions disposed along facing edges of the electrodes separate the level at which tissue is electrically contacted by the electrodes from the level at which tissue is sheared by the cutting blades.

11 Claims, 2 Drawing Sheets

U.S. PATENT DOCUMENTS

| | | |
|---|---|---|
| 5,908,420 A | 6/1999 | Parins et al. |
| 5,954,720 A | 9/1999 | Wilson et al. |
| 5,967,997 A | 10/1999 | Turturro et al. |
| 5,976,130 A | 11/1999 | McBrayer et al. |
| 6,024,744 A | 2/2000 | Kese et al. |
| 6,090,108 A | 7/2000 | McBrayer et al. |
| 6,179,837 B1 * | 1/2001 | Hooven ....................... 606/50 |
| 6,206,872 B1 | 3/2001 | Lafond et al. |
| 6,283,963 B1 | 9/2001 | Regula |
| 6,299,630 B1 | 10/2001 | Yamamoto |
| 6,355,035 B1 | 3/2002 | Manushakian |
| 6,749,609 B1 * | 6/2004 | Lunsford et al. ............. 606/51 |

* cited by examiner

ELECTROCAUTERY SURGICAL SCISSORS

RELATED APPLICATIONS

This is application is a continuation of application Ser. No. 10/071,940, entitled "Electrocautery Surgical Scissors," filed on Feb. 5, 2002 by J. Lunsford et al., and now issued as U.S. Pat. No. 6,749,609. The subject matter of this application relates to the subject matter described in application Ser. No. 09/739,595 entitled "Elongated Surgical Scissors," filed on Dec. 15, 2000 by T. Chang et al., now issued as U.S. Pat. No. 6,506,207, which subject matter is incorporated herein by this reference.

FIELD OF THE INVENTION

This invention relates to surgical instruments incorporating scissors and to surgical scissors, and more particularly to surgical scissors having electrocautery electrodes disposed adjacent tissue-cutting blades for selective cauterization and shearing of tissue.

BACKGROUND OF THE INVENTION

Endoscopic surgery commonly requires manual manipulation of surgical instruments that are introduced into a surgical site within a patient through elongated cannulas containing one or more interior lumens of slender cross section. Endoscopic surgery to harvest a saphenous vein usually involves an elongated cannula that is advanced along the course of the vein from an initial incision to form an anatomical space about the vein as connective tissue is dissected away from the vein.

Lateral branch vessels of the saphenous vein can be conveniently isolated and ligated within the anatomical space under endoscopic visualization using surgical scissors that can be positioned and manipulated through the elongated cannula. Such surgical procedures are commonly employed in the preparation of the saphenous vein for removal from within the anatomical space for use, for example, as a shunting or graft vessel in coronary bypass surgery.

Surgical scissors that are used to transect vessels within the confines of limited anatomical space formed along the course of the saphenous vein commonly incorporate electrodes on or near the tissue-shearing blades. Scissors of this type are suitable for monopolar or bipolar electrocauterization of tissue prior to transection of, for example, lateral side branches of the saphenous vein to be harvested. However, placement of the electrodes in relation to the tissue-shearing edges of the blades may inhibit proper operation of the blades to shear tissue and may inhibit thorough electrocauterization of a side branch vessel as the blades close during transection of the vessel.

SUMMARY OF THE INVENTION

In accordance with the present invention, surgical scissors include scissor blades mounted at the distal end of a slender body for manual manipulation under control of a lever mounted at the proximal end of the slender body. The scissor blades support electrodes that are positioned to supply electrical energy from external sources to cauterize tissue prior to shearing the cauterized tissue at a remote surgical site in a patient. The electrodes of various configurations are spaced from, and are electrically isolated from, the tissue-cutting blades (or at least from one such blade) in order to optimize both the ability to shear tissue as well as the ability to localize the electrocauterization of the tissue to be sheared within a wide angle of alignment of tissue relative to the blade.

Surgical scissors in accordance with the present invention may be incorporated into and form an integral part of more comprehensive surgical apparatus, for example, as illustrated and described with reference to FIGS. 8 and 9 of pending application Ser. No. 10/054,477, entitled "Vessel Harvesting Apparatus and Method", filed on Jan. 18, 2002 by M. Stewart et al.

DESCRIPTION OF THE INVENTION

Figure 1:
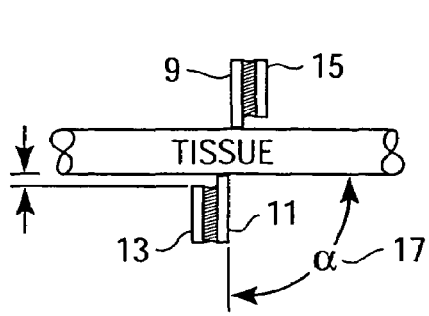
FIG. 1 is a partial sectional view of conventional bipolar surgical scissors.

Referring now to FIG. 1, there is shown a cross-sectional end view of conventional surgical scissors that include both shearing blades 9, 11 and electrically-conductive blade supports 13, 15 that carry in insulated manner the respective cutting blades 9, 11. In this configuration, the cutting blades 9, 11 are positioned against tissue (typically a lateral or side branch vessel of a main vessel such as a saphenous vein) in preparation for cutting the tissue prior to or coincident with contact being made with the tissue by the blade supports serving as electrodes 13, 15. As a result, electrocauterization of the tissue is not possible until either the cutting blades 9, 11 penetrate tissue sufficiently to engage the electrodes 13, 15, or the angle 17 of presentation of the tissue to the cutting blades 9, 11 is skewed sufficiently (by an obtuse angle in the illustration) for the electrodes 13, 15 to contact the tissue prior to contact therewith by the shearing blades 9, 11, or the tissue is manipulated to conform to the irregular surfaces by pressing the scissors against the tissue.

Figure 2:
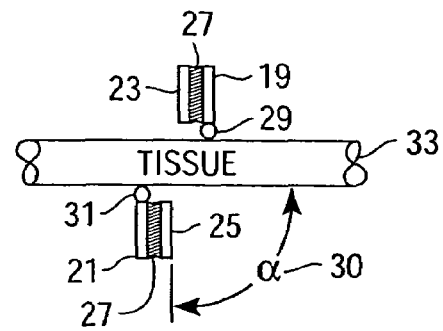
FIGS. 2, 3 and 4 are partial sectional views of embodiments of bipolar scissors in accordance with the present invention.
Figure 3:
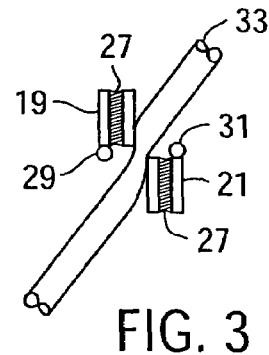
Figure 4:
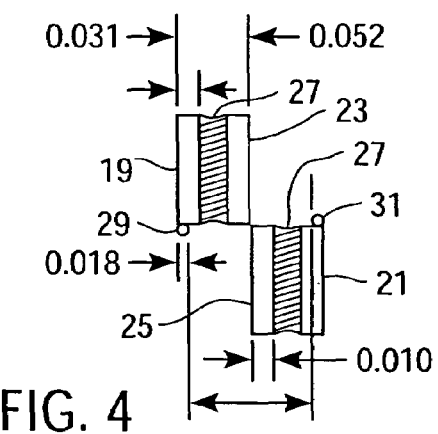

In accordance with one embodiment of the present invention as illustrated in FIG. 2, an outer set of blade supports 19, 21 serve as bipolar electrodes and also support respective cutting blades 23, 25 via insulated attachment 27 to the inner or facing surfaces of the blade supports 19, 21. A mixture of tiny glass beads and epoxy provide a suitable insulating and attaching layer 27 for securing the blades 23, 25 to the respective blade supports 19, 21. The cutting blades 23, 25 are thus disposed to pass by each other along an advancing point of contact along the contiguous cutting edges as the blades 23, 25 move toward and past each other in scissor-like manner. The blade supports 19, 21 each include a conductive extension 29, 31 that protrudes inwardly toward the opposite blade support to elevate the level or points of contact thereof with tissue above the level or points of contact of the cutting blades 21, 23 with the tissue. In this configuration, the angle 30 of presentation of the tissue to the cutting blades 23, 25 and electrodes 19, 21 within which electrical contact can be made to tissue prior to contact therewith by the cutting blades is much broader, to an extreme limit as illustrated in FIG. 3. This facilitates the surgeon positioning such bipolar scissors relative to a side branch vessel 33 at a diversity of angles for electrocauterizing and then transecting the vessel. In preferred embodiments, various configurations of extensions 29, 31 on each of the electrodes 19, 21 extend in directions toward the opposite ones of the electrodes to elevate the level of electrical contacts with tissue by about 0.018" to about 0.030" above the level of the cutting edges of the blades 23, 25, as illustrated in the sectional views of FIGS. 2-6. The electrode extensions 29 in these various illustrated embodiments may be welded onto the facing edges of the electrodes 19, 21 that serve as blade supports for the respective cutting blades 23, 25, or may be formed as part of the electrode-blade support 19, 21, as shown in the plan views of FIGS. 8a and 8b.

Figure 5:
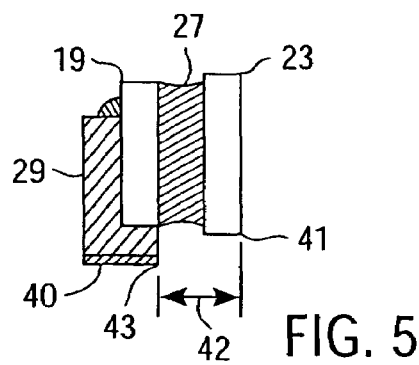
FIGS. 5 and 6 are partial sectional views of other embodiments of bipolar scissors in accordance with the present invention.

Referring now to FIG. 5, the L-shaped extension 29 on the blade support 29, as shown in sectional view, is welded or otherwise conductively joined to each blade support 19. The tissue-contacting edge 40 is thus elevated by about 0.018" to about 0.030" while also reducing the spacing 42 between the inside edge of the electrode 43 and the cutting edge 41 of cutting blade 23. This increases the angle of presentation of the tissue to the cutting blades, as previously described with reference to FIG. 3. Of course, similar extensions 29 may be attached in mirror symmetry to each of the blade supports of a scissor structure in accordance with the present invention to enhance the angle of presentation of tissue to the cutting blades.

Figure 6:
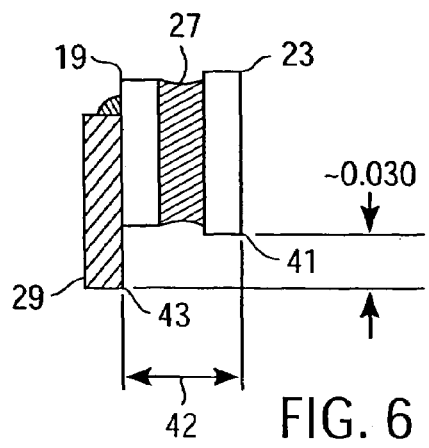

Referring now to FIG. 6, there is shown a sectional view of another conductive extension 29 that is conductively attached to the back side of the blade support 19. In this configuration, the inside edge 41 of the cutting blade 23 is spaced 42 from the protruding inside edge of the extension 29 at a distance that allows tissue to be compressed in cauterizing or cutting action in conformity with irregular surfaces involved. Specifically, this structure facilitates presentation of tissue to the cutting edge 41 of the blade 23 at an angle of approximately 90° for optimized cutting and cauterizing operation.

Figure 7:
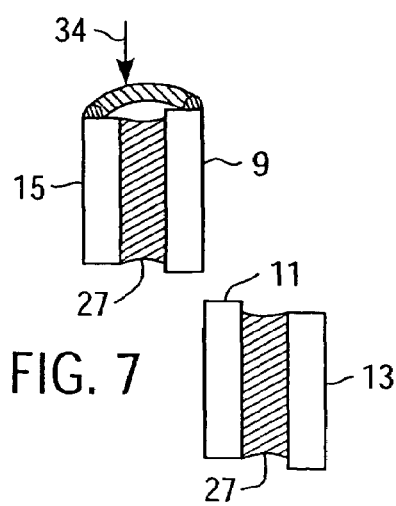
FIG. 7 is a partial sectional view of bipolar scissors modified in accordance with the present invention.

Referring now to the sectional view of FIG. 7, conventional bipolar scissor blades 9, 11 that commonly extend inwardly or beyond the tissue-contacting edge of the attached electrodes 13, 15 may be electrically configured differently to broaden the angle of presentation within which bipolar electrodes 9, 15 and 13 may first contact tissue prior to the blades 9, 11 making tissue-shearing contact. Specifically, electrode 15 and blade 9 are electrically coupled together 34 to circumvent the electrical insulating properties of layer 27, while the electrode 13 of one polarity remains electrically insulated from the structure of blades 9, 11 and electrode 15 of opposite polarity. This configuration enhances the benefit of the blade 9, serving as an electrode, protruding inwardly toward the opposite electrode 13, and thus enhances the angle of presentation within which tissue such as a side branch vessel may be oriented relative to the blades and electrodes for electrocauterization prior to transection of the vessel.

This configuration also facilitates formation of current conduction paths through tissue in contact with the structure, for example, from blade support or electrode 13 to the cutting blade 11, or cutting blade 9 or to blade support 15. Alternatively, the structure of blade support 15 and insulating layer 27 and cutting blade 9 and conductive link 34 can be configured as a single conductive cutting blade.

Figure 8A:
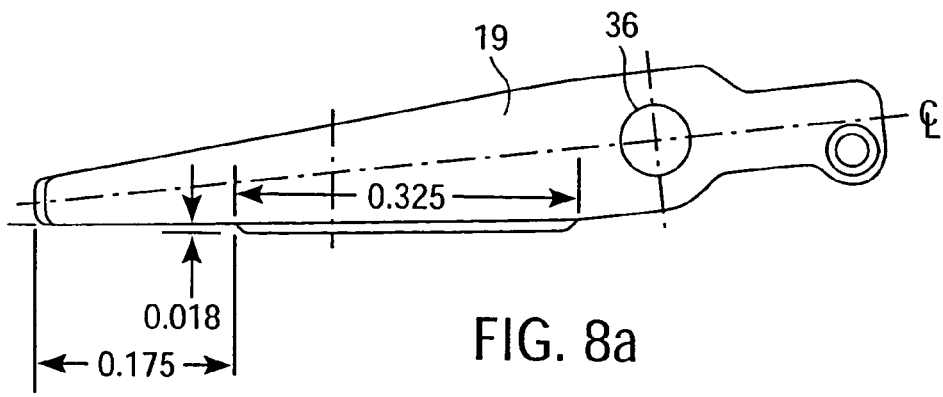
FIGS. 8a and 8b are plan views of a set of bipolar scissor blades in accordance with the present invention.
Figure 8B:
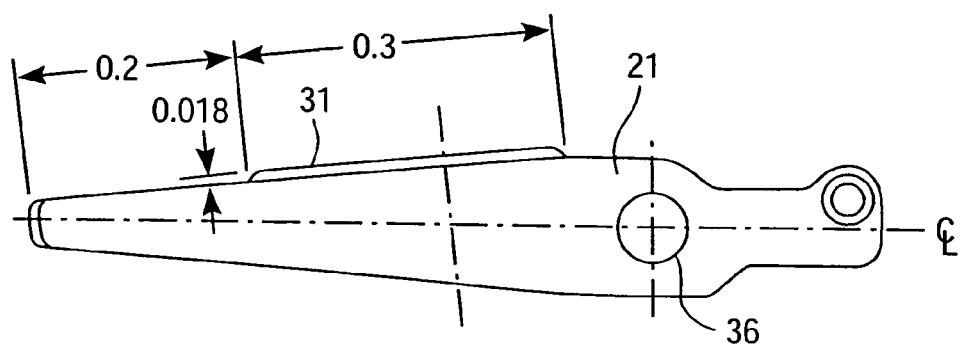
Figure 9:
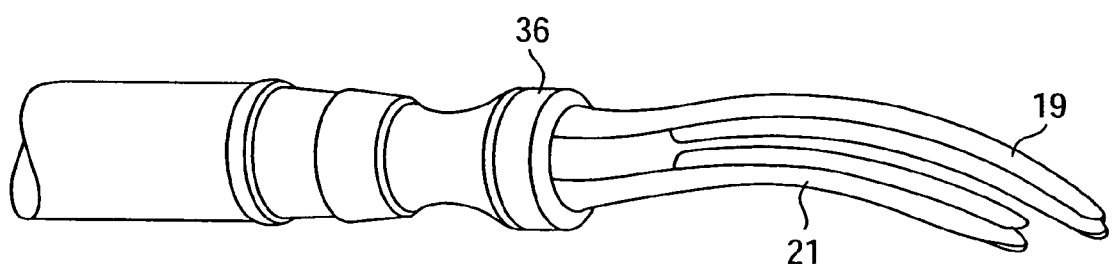
FIG. 9 is a pictorial side view of an embodiment of the bipolar scissor blades according to FIGS. 8a and 8b.

Referring now to FIGS. 8a and 8b, there are shown plan views of a complementary set of left and right electrode-blade supports 19, 21 that include respective extensions or protrusions 29, 31 from the facing edges thereof. These extensions or protrusions 29, 31 protrude by about 0.018" and extend along about ⅔, or a major portion, of the proximal sections of the facing edges relative to pivot axes 36. Of course, the extensions or protrusions from the facing edges may extend out to the distal ends of the associated supports. This configuration expands the angle of presentation of tissue to the blades and electrodes within which electrocauterizing contact with the tissue occurs prior to shearing contact therewith, for reasons as previously described herein, as the electrode-blade supports 19, 21 are rotated about the pivot axes 36 toward each other in scissor-like manner. These electrodes 19, 21 and associated cutting blades 23, 25 may be curved, as shown in FIG. 9, and the cutting edges of curved blades attached thereto may be serrated to enhance tissue-cutting capability.

Figure 10:
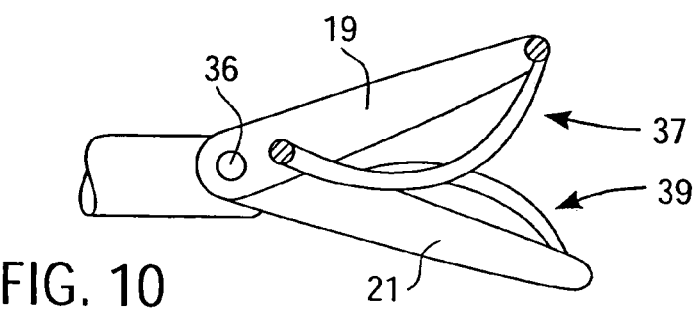
FIG. 10 is a partial side view of another embodiment of bipolar scissors in accordance with the present invention.

In another embodiment as illustrated in FIG. 10, the electrode-blade supports 19, 21 include arcuate conductive members 37, 39 welded to, or otherwise electrically and mechanically attached to, the outer surfaces or facing edges of the electrodes 19, 21. Such arcuate members 37, 39 facilitate electrical contact with tissue such as a side-branch vessel over a wide range of presentation angles relative to the electrodes 19, 21. Cutting blades (not shown in FIG. 10) may be attached in insulated manner to the inside facing surfaces of the electrodes 19, 21 in the manner as previously described herein to facilitate cutting tissue following electrocauterization during the closing of the electrodes in scissor-like manner about the pivot axis 36.

Therefore, the bipolar tissue-cauterizing and cutting instruments according to the present invention provide reliable electrical contact with tissue to be cut over a broad range of angles of presentation of the tissue to the electrodes. This assures controlled electrocauterization prior to shearing or transection of the cauterized tissue. Various configurations of blade supports that serve as electrodes and that support cutting blades in facing, scissor-like engagement along contiguous cutting edges assure reliable electrical contact for electrocauterization of tissue prior to shearing of the cauterized tissue.

What is claimed is:

1. Tissue-cutting apparatus comprising:

first and second electrically conductive tissue-cutting blades coupled together about a common pivot for relative movement thereabout between open and closed positions, the first and second tissue-cutting blades, each having an elongated cutting edge with the cutting edges disposed to pass each other in contiguous relationship along the elongated cutting edges as the first and second relatively move from open toward closed positions;

an electrode disposed on and insulated from each of the first and second blades on a side thereof remote from the contiguous cutting edges;

an electrical connection between only one of the first and second blades and the associated electrode disposed thereon for establishing common electrical signal potential thereon, the electrode on at least one of the first and second tissue-cutting blades being extended with respect to the cutting edge of the associated blade in a direction toward the cutting edge of the other of the first and second tissue-cutting blades; and conductors connected to the electrodes for supplying electrical signals thereto.

2. Tissue-cutting apparatus according to claim 1 in which the electrodes on each of the first and second tissue-cutting blades is extended with respect to the cutting edge of the associated blade in a direction toward the cutting edge of the other of the first and second tissue-cutting blades.

3. Tissue-cutting apparatus comprising:
a pair of conductive cutting blades mounted for rotation about a common pivot between open and closed configurations with cutting edges of the cutting blades disposed to pass each other in contiguous relationship along elongated portions of the cutting edges in response to movement of the pair of cutting blades about the common pivot; and
an electrode attached to and insulated from each of the cutting blades with only one of the electrodes connected to the associated cutting blade, the electrode on at least one of the cutting blades being extended with respect to the cutting edge of the associated blade in a direction toward the cutting edge of the other cutting blade.

4. Tissue-cutting apparatus according to claim 3 in which the electrodes on each of the cutting blades is extended in a direction toward each other.

5. Tissue-cutting apparatus according to claim 3 in which an electrically-conductive electrode extension is disposed on each of the pair of cutting blades at locations thereon spaced from the cutting edges thereof and extended with respect thereto in a direction toward the other of the cutting edges.

6. Tissue-cutting apparatus according to claim 5 in which the electrode extensions have facing edges disposed to contact tissue prior to the cutting edges contacting tissue during movement of the first and second cutting blades toward the closed configuration.

7. Tissue cutting apparatus according to claim 5 in which the electrode extensions extend along less than the entire length of the cutting edges proximal the pivot.

8. Tissue-cutting apparatus according to claim 7 in which the electrode extension extend along about ⅔ of the length of the cutting edges proximal the pivot.

9. Tissue-cutting apparatus according to claim 5 in which each electrode extension includes an arcuate member electrically attached to the respective cutting blade with convex arcuate surfaces thereof facing each other and disposed to pass by each other in response to movement of the respective cutting blades about the pivot.

10. Tissue-cutting apparatus comprising:
first and second electrically conductive cutting blades coupled together about a pivot for relative movement thereabout between open and closed positions, each of the first and second conductive cutting blades having an elongated cutting edge disposed to pass each other in contiguous and conductive relationship along the elongated cutting edges as the first and second cutting blades relatively move from open toward closed positions;
electrodes attached to and insulated from the cutting blades and disposed to receive opposite-potential electrical signals supplied thereto, the electrode on each of the first and second tissue-cutting blades being extended with respect to the cutting edge of the associated blade in a direction toward the cutting edge of the other of the first and second tissue-cutting blades; and
a conductor electrically connecting only one of the cutting blades to the attached electrode for energizing both tissue-cutting blades and the one electrode with an opposite potential than the other electrode.

11. Tissue-cutting apparatus according to claim 10 further including a layer of insulation between the one electrode and its attached tissue-cutting blade with the conductor bridging the layer of insulation.

* * * * *